(12) United States Patent
Wada et al.

(10) Patent No.: US 8,168,145 B2
(45) Date of Patent: May 1, 2012

(54) POROUS TITANIUM OXIDE AND PROCESS FOR PRODUCING THE SAME

(75) Inventors: Masayoshi Wada, Yokohama (JP); Shoichiro Shio, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 445 days.

(21) Appl. No.: 12/443,186

(22) PCT Filed: Sep. 21, 2007

(86) PCT No.: PCT/JP2007/068410
§ 371 (c)(1),
(2), (4) Date: Mar. 27, 2009

(87) PCT Pub. No.: WO2008/038592
PCT Pub. Date: Apr. 3, 2008

(65) Prior Publication Data
US 2010/0009192 A1      Jan. 14, 2010

(30) Foreign Application Priority Data

Sep. 28, 2006  (JP) .................................. 2006-263832

(51) Int. Cl.
*C01G 23/00* (2006.01)
(52) U.S. Cl. ............... 423/81; 423/82; 423/84; 423/610
(58) Field of Classification Search .................... 423/81, 423/82, 84, 610
See application file for complete search history.

(56) References Cited

U.S. PATENT DOCUMENTS

| | | | |
|---|---|---|---|
| 3,825,438 A * | 7/1974 | Pritchard | ...................... 427/218 |
| 6,187,438 B1 | 2/2001 | Chopin et al. | |
| 2003/0082122 A1 | 5/2003 | Chopin et al. | |
| 2005/0079367 A1 | 4/2005 | Ohmori et al. | |
| 2006/0188432 A1 | 8/2006 | Shio | |

FOREIGN PATENT DOCUMENTS

| | | | |
|---|---|---|---|
| DE | 10 2006 020961 A1 | 11/2007 | |
| EP | 1 873 011 A2 | 1/2008 | |
| EP | 2 039 990 A1 | 3/2009 | |
| FR | 2753980 | 4/1998 | |
| JP | 55-10428 | 1/1980 | |
| JP | 2-196029 | 8/1990 | |
| JP | 11-157839 | 6/1999 | |
| JP | 2003-192349 | 7/2003 | |
| JP | 2003-246620 | 9/2003 | |
| JP | 2004-292266 | 10/2004 | |
| JP | 2006-89297 | 4/2006 | |
| KR | 2002-043133 | * | 6/2002 |
| WO | WO 2006/097067 A1 | 9/2006 | |
| WO | WO 2007/027474 | 3/2007 | |

OTHER PUBLICATIONS

Abstract of KR 2002043133A, Choi et al., Jun. 8, 2002.*
Japanese Patent Abstract Publication No. 02-196029 published Aug. 2, 1990, one page.
Japanese Patent Abstract Publication No. 11-157839 published Jun. 15, 1999, seven pages.
Japanese Patent Abstract Publication No. 55-010428 published Jan. 24, 1980, one page.
Japanese Patent Abstract Publication No. 2003-192349 published Jul. 9, 2003, 15 pages.
Japanese Patent Abstract Publication No. 2006-089297 published Apr. 6, 2006, 11 pages.
International Search Report for PCT/JP2007/068410 mailed Oct. 30, 2007, two pages.
Japanese Abstract for Publication No. 2006-089297 published Apr. 6, 2006, 10 pages.
Japanese Abstract for Publication No. 2003-246620 published Sep. 2, 2003, 11 pages.
Supplementary European Search Report for Application No. EP07807742 mailed Jun. 7, 2010, six pages.

* cited by examiner

Primary Examiner — Steven Bos
(74) *Attorney, Agent, or Firm* — Rankin, Hill & Clark LLP

(57) ABSTRACT

The present invention provides a porous titanium oxide having improved ultraviolet protection ability, usability, and transparency in the visible region and a process for producing thereof. The porous titanium oxide powder according to the present invention can be obtained by adding an alkali to a titanium salt solution containing a polyalcohol and then thermally hydrolyzing the solution. In addition, it is possible that after the addition of the alkali, an acid is further added to the solution and then the thermal hydrolysis is conducted, or that after thermal hydrolysis, further heat treatment with an acid is conducted. A porous titanium oxide has a mean particle size of 0.01 to 1.0 μm and a specific surface area of 50 $m^2/g$ or more.

9 Claims, 1 Drawing Sheet

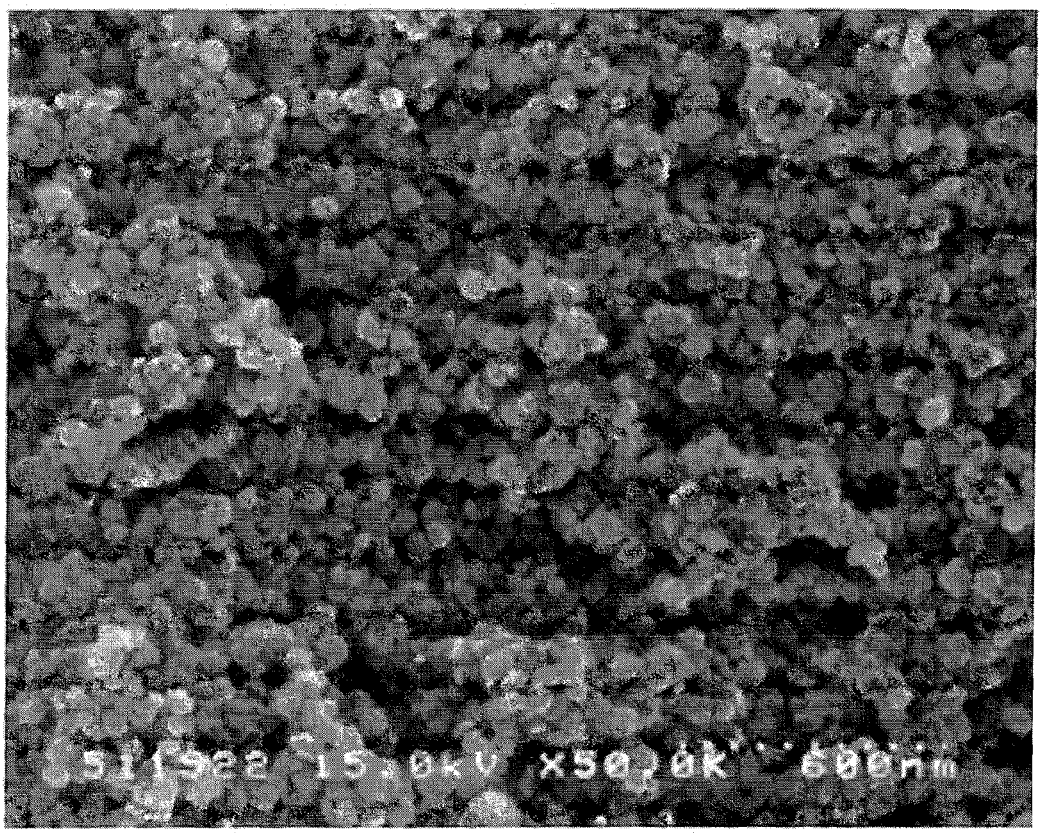

POROUS TITANIUM OXIDE AND PROCESS FOR PRODUCING THE SAME

RELATED APPLICATIONS

The present application claims the priority of Japanese Patent Application No. 2006-263832 filed on Sep. 28, 2006, which is incorporated herein by reference.

FIELD OF THE INVENTION

The present invention relates to a porous titanium oxide and a process for producing it, particularly its ultraviolet protection ability, transparency, usability, and the like.

BACKGROUND OF THE INVENTION

Titanium oxide has a high refractive index and excellent covering power, coloring ability, and ultraviolet protection ability. Thus it has traditionally been widely used as a pigment in products such as paint, plastics, and cosmetics. Titanium oxide contained in bases for these products as an ultraviolet protective agent is commonly fine particle powder having a mean primary particle size of 0.1 μm or less, which is a result of the pursuit of ultraviolet protection ability and transparency. Examples of known processes for producing titanium oxide include a method of thermally hydrolyzing titanyl sulfate or titanium tetrachloride in the aqueous phase and a method of neutralizing and hydrolyzing such a compound (see Patent Document 1, for example).

However, because of its very small particle size, such fine particle powder has high oil absorption and easily aggregates: thus it is difficult to disperse such powder in a product base. In addition, products such as cosmetics containing the fine particle powder provide a high ultraviolet protective effect in the UV-B region (280 to 320 nm) while they have problems such as poor transparency in the visible region (400 to 700 nm) and roughness and poor spreadability in actual use.

Patent Document 2 discloses that a porous titanium oxide powder can be obtained by thermally hydrolyzing a titanium salt solution in the presence of an aliphatic alcohol and then further heat treating the solution with an acid.

This porous titanium oxide has an excellent ultraviolet protective effect, usability, and transparency in the visible region, but it is desirable to further improve these properties.

Patent Document 1: Japanese Unexamined Patent Publication No. 55-10428
Patent Document 2: Japanese Unexamined Patent Publication No. 2004-292266

DISCLOSURE OF THE INVENTION

Problem to be Solved by the Invention

The present invention has been made in view of the problems described in the background art, and an object of the invention is to provide a porous titanium oxide having improved ultraviolet protection ability, usability, and transparency in the visible region and a process for producing thereof.

Means to Solve the Problem

To achieve the object, the present inventors have conducted extensive studies and found that a porous titanium oxide can be obtained by adding an alkali to a titanium salt solution containing an aliphatic alcohol and then thermally hydrolyzing the solution and that this porous titanium oxide has very high ultraviolet protection ability, usability, and transparency in the visible region. The inventors have also found that these properties can be further improved by further addition of an acid after adding the alkali and/or by heat treatment with an acid after thermal hydrolysis. Thus the present invention has been accomplished.

That is, the process for producing the porous titanium oxide according to the present invention is characterized by comprising steps of:

adding an alkali to a titanium salt solution containing a polyalcohol; and thermally hydrolyzing the solution.

In the invention, it is preferable that the after the alkali is added to the titanium salt solution, an acid is further added thereto and then the solution is thermally hydrolyzed.

In the invention, it is preferable that the molar ratio of the amount of the alkali added with respect to that of the titanium salt is 0.1:1 to 1:1.

In the invention, it is preferable that the molar ratio of the amount of the acid added with respect to that of the titanium salt is 0.1:1 to 1:1.

In the invention, it is preferable that after the thermal hydrolysis, a heat treatment with an acid is further conducted.

In the invention, it is preferable that the molar ratio of the amount of the polyalcohol to that of the titanium salt is 0.1:1 to 5:1.

The porous titanium oxide according to the invention is a porous titanium oxide obtained by any of the processes mentioned above, and has a mean particle size of 0.01 to 1.0 μm and a specific surface area of 50 $m^2/g$ or more.

The cosmetic preparation according to the invention is characterized by comprising the porous titanium oxide mentioned above.

Effect of the Invention

According to the present invention, a porous titanium oxide having very high ultraviolet protective effect and transparency and excellent usability can be obtained.

BRIEF DESCRIPTION OF THE DRAWINGS

FIG. 1 is a photomicrograph of the porous titanium oxide powder of an example according to the present invention observed under a scanning electron microscope (SEM).

BEST MODE FOR CARRYING OUT THE INVENTION

The porous titanium oxide powder according to the present invention can be obtained by adding an alkali to a titanium salt solution containing a polyalcohol and then thermally hydrolyzing the solution. The addition of the alkali improves the ultraviolet protective effect and transparency of the porous titanium oxide obtained.

The alkali used is not particularly limited, but sodium hydroxide, potassium hydroxide, ammonia water, sodium carbonate, or the like is preferably used. It is preferable that the molar ratio of the amount of the alkali added with respect to that of the titanium salt is 0.1:1 to 1:1. If the amount of the alkali is too small, its effect will become insufficiently while if the amount is too high, the particles will become too fine and aggregate excessively, resulting in reduced ultraviolet protective effect and transparency.

The solution is mixed thoroughly after the alkali is added. For example, the solution is stirred at 10 to 40° C. for 10 minutes to 24 hours, preferably at 20 to 40° C. for 10 to 60 minutes.

In addition, when after the addition of the alkali, an acid is further added to the solution and then the thermal hydrolysis is conducted, a porous titanium oxide having much higher ultraviolet protective effect can be obtained.

Such an acid is not particularly limited, but hydrochloric acid, sulfuric acid, nitric acid, or the like is preferably used, and hydrochloric acid is particularly preferable. The molar ratio of the amount of the acid added with respect to that of the titanium salt is preferably 0.1:1 to 1:1. If the amount of the acid added is too small, its effect will become insufficiently while if the amount is too high, the acid inhibits hydrolysis too much and thus the particles will become too fine and aggregate excessively, and the yield will be reduced.

The solution is mixed thoroughly after the acid is added. For example, the solution is stirred at 10 to 40° C. for 10 minutes to 24 hours, preferably at 20 to 40° C. for 10 to 60 minutes.

In the present invention, a polyalcohol is made present in the titanium salt solution. If no polyalcohol is used, even when an alkali and an acid are added as mentioned above and then the solution is thermally hydrolyzed, the ultraviolet protective effect and transparency of the porous titanium oxide obtained will be extremely low.

The polyalcohol used is not particularly limited, but ethylene glycol, propylene glycol, 1,3-butylene glycol, glycerol, erythritol, xylitol, mannitol, sorbitol, maltitol, or the like is preferably used. Although a porous titanium oxide can be obtained even with a monohydric alcohol, the porous titanium oxide obtained does not have as good a shape as with a polyalcohol. A particularly preferable polyalcohol is glycerin.

The molar ratio of the amount of the polyalcohol added with respect to that of the titanium salt is normally 0.1:1 to 5:1, preferably 0.5:1 to 2.5:1. If the amount added is too small or too high, it is difficult to obtain a porous titanium oxide producing a good effect.

The solution is mixed thoroughly after the polyalcohol is added. For example, the solution should be stirred at 10 to 40° C. for 10 minutes to 24 hours, preferably at 20 to 40° C. for 5 to 20 hours.

The starting material of the titanium salt solution used in the present invention is not particularly limited, but an aqueous solution of an inorganic titanium salt such as titanium sulfate, titanyl sulfate, titanium tetrachloride, or the like is preferably used. As the starting material, an organic titanium salt such as titanium tetraisopropoxide can also be used. The concentration of the titanium salt solution is preferably 0.1 to 5 mol/L.

The thermal hydrolysis conditions are appropriately determined based on the type and concentration of the titanium salt solution and additives used and the like. Normally, the thermal hydrolysis is preferably conducted at 50 to 100° C. for 1 to 12 hours.

In addition, in the present invention, thermal hydrolysis followed by further heat treatment with an acid further improves the ultraviolet protective effect and the transparency in the visible region.

For example, the acid heat treatment may be conducted as follows: the residue obtained by filtration after the thermal hydrolysis is resuspended in water to produce slurry, and an acid is added to the slurry, and then the slurry is heated. Alternatively, the residue is resuspended in an aqueous solution of an acid and then the slurry is heated.

Examples of such acids include sulfuric acid, nitric acid, and hydrochloric acid, and hydrochloric acid is preferable. The molar ratio of the amount of the acid added in the acid heat treatment with respect to that of the titanium in the slurry can normally be 1:1 to 8:1.

The heating conditions may be appropriately determined based on the starting materials, additives, and concentrations used and the like, and they are normally ranges similar to those of the thermal hydrolysis conditions.

It is preferable that after the acid heat treatment, the solution is neutralized with an alkali and then filtered, washed with water, and dried. In addition, the dried material may be calcined, if necessary.

The titanium oxide powder obtained in the present invention is pseudospherical (approximately spherical) porous particles, which are formed by the aggregation of primary particles of titanium oxide. By SEM observations, the mean particle size of the porous particles ranges from 0.01 to 1 μm, and in terms of ultraviolet protection ability and transparency, preferably from 0.03 to 0.15 μm. The specific surface area (BET) is 50 $m^2$/g or more.

The porous titanium oxide powder obtained in the present invention has very high transparency and ultraviolet protective effect. This seems to be because the titanium oxide powder is hard to aggregate with its good dispersibility in bases and as well as the titanium oxide powder is porous. In addition, the porous titanium oxide powder according to the invention is pseudospherical, resulting in excellent usability without roughness.

In the present invention, a substance having a carboxyl group or a carbonyl group may be made present with a polyalcohol. In this case, the porous powder tends to have a smaller particle size than in the case where such a substance is not used together.

Such a substance is not limited unless it particularly interferes, but it is preferably an aliphatic compound having a carbon number of 1 to 22. Typical examples of the compound include an aliphatic carboxylic acid or a derivative thereof. As such an aliphatic carboxylic acid, monobasic acids such as formic acid, acetic acid, propionic acid, caprylic acid, and stearic acid, dibasic acids such as oxalic acid, succinic acid, and adipic acid, or higher polybasic acids can be used. Typical examples of such a derivative include salts such as alkali metal salts, alkaline earth metal salts, and quaternary ammonium salts and esters such as methyl ester and ethyl ester. Amino acids, amides, and the like can also be used unless they particularly interfere. Preferable examples of carboxylic acids or derivatives thereof include carboxylic acid and their salts and esters. Acetic acid is particularly preferable.

The amount of a substance having a carboxyl group or a carbonyl group added may be appropriately determined based on the type thereof and other conditions, and normally the molar ratio of the amount of the substance with respect to that of the titanium is preferably 0.1:1 to 5:1, more preferably 0.5:1 to 3:1. If the amount added is too small, the effect will not be produced while if the amount added is too much, the particles will become too fine, inducing aggregation.

Titanium oxide is known to act as a photocatalyst when the titanium oxide is exposed to light, particularly ultraviolet light.

On the other hand, if titanium oxide is added to any bases, this photocatalysis can change properties of other components contained in the base. To avoid this change, surface treatment can be applied to the titanium oxide powder. In the fields such as cosmetics, surface treatment is preferably applied to make them water-repellent as well.

The surface treatment used in the present invention is not particularly limited. Examples of such surface treatments include aluminum treatment, silicone treatment, fatty acid soap treatment, dextrin fatty acid ester treatment, and fluorine treatment. In addition, it can be expected that the ultraviolet absorption properties can be changed by further covering the surface with other metal species.

The porous titanium powder according to the present invention is thermally and chemically stable. It is possible to add oils, water, powders, surfactants, lower alcohols, polyalcohols, humectants, antiseptics, polymers, antioxidants, perfumes, various drugs, and the like to the porous titanium powder in the qualitative and quantitative ranges that do not impair effects of the present invention such as ultraviolet protection.

If the porous titanium oxide powder according to the present invention is added to cosmetics, the forms of the cosmetics are not particularly limited, and can take various forms such as powder form, cream form, stick form, pencil form, and liquid form depending on the intended use. It is possible to provide various cosmetics such as makeup bases, foundations, face powders, cheek colors, lipsticks, mascaras, eye shadows, eyeliners, creams, milky lotions, and skin lotions. These cosmetics, along with the porous titanium oxide according to the invention, can be produced using ingredients that can be normally added to cosmetics, by means of a known method.

EXAMPLES

Production Example 1

To 1 L of a 1 mol/L aqueous solution of titanium tetrachloride was added 92 g (1 mol) of glycerin, and the resulting mixture was stirred at 40° C. 10 g (0.25 mol) of sodium hydroxide was added to the mixture and further stirred at 40° C. for 30 minutes. To the resulting mixture was further added 26 g (0.25 mol) of 35% hydrochloric acid. After being stirred at 40° C. for 30 minutes, the resulting mixture was thermally hydrolyzed at 90° C. for 3 hours and then filtered. The filtration residue was washed with water and dried to obtain an anatase titanium oxide powder.

SEM observations showed that the powder obtained was porous pseudospherical particles having a mean particle size of about 70 nm, which had been formed by the aggregation of primary particles of titanium oxide. In addition, the specific surface area was 182 $m^2/g$.

Production Example 2

After the thermal hydrolysis in Production Example 1, the solution was further heat treated with an acid. More specifically, to 1 L of a 1 mol/L aqueous solution of titanium tetrachloride was added 92 g (1 mol) of glycerin, and the resulting mixture was stirred at 40° C. 10 g (0.25 mol) of sodium hydroxide was added to the mixture and further stirred at 40° C. for 30 minutes. To the resulting mixture was further added 26 g (0.25 mol) of 35% hydrochloric acid. After being stirred at 40° C. for 30 minutes, the resulting mixture was thermally hydrolyzed at 90° C. for 3 hours.

Next, after the resulting sol was filtered, the filtration residue was dispersed in 500 mL of 1.5 mol/L hydrochloric acid with an ultrasonic disperser, stirred at 90° C. for 3 hours, neutralized with sodium hydroxide, and then filtered. The filtration residue was washed with water and dried to obtain an anatase titanium oxide powder.

SEM observations showed that the powder obtained was porous pseudospherical particles having a mean particle size of about 60 nm, which had been formed by the aggregation of primary particles of titanium oxide. In addition, the specific surface area was 343 $m^2/g$.

Production Example 3

This example was produced without adding any acid after alkali addition in Production Example 2. More specifically, to 1 L of a 1 mol/L aqueous solution of titanium tetrachloride was added 92 g (1 mol) of glycerin, and the resulting mixture was stirred at 40° C. 10 g (0.25 mol) of sodium hydroxide was added to the mixture and further stirred at 40° C. for 30 minutes. The resulting mixture was thermally hydrolyzed at 90° C. for 3 hours.

Next, after the resulting sol was filtered, the filtration residue was dispersed in 500 mL of 1.5 mol/L hydrochloric acid with an ultrasonic disperser, stirred at 90° C. for 3 hours, neutralized with sodium hydroxide, and then filtered. The filtration residue was washed with water and dried to obtain an anatase titanium oxide powder.

SEM observations showed that the powder obtained was porous pseudospherical particles having a mean particle size of about 70 nm, which had been formed by the aggregation of primary particles of titanium oxide.

Production Example 4

This example was produced by using acetic acid instead of hydrochloric acid in Production Example 2. More specifically, to 1 L of a 1 mol/L aqueous solution of titanium tetrachloride was added 92 g (1 mol) of glycerin, and the resulting mixture was stirred at 40° C. 10 g (0.25 mol) of sodium hydroxide was added to the mixture and further stirred at 40° C. for 30 minutes. To the resulting mixture was further added 60 g (1 mol) of acetic acid. After being stirred at 40° C. for 30 minutes, the resulting mixture was thermally hydrolyzed at 90° C. for 3 hours.

Next, after the resulting sol was filtered, the filtration residue was dispersed in 500 mL of 1.5 mol/L hydrochloric acid with an ultrasonic disperser, stirred at 90° C. for 3 hours, neutralized with sodium hydroxide, and then filtered. The filtration residue was washed with water and dried to obtain an anatase titanium oxide powder.

SEM observations showed that the powder obtained was porous pseudospherical particles having a mean particle size of about 60 nm, which had been formed by the aggregation of primary particles of titanium oxide.

Production Example 5

This example was produced by using acetic acid together with hydrochloric acid in Production Example 2. More specifically, to 1 L of a 1 mol/L aqueous solution of titanium tetrachloride was added 92 g (1 mol) of glycerin, and the resulting mixture was stirred at 40° C. 10 g (0.25 mol) of sodium hydroxide was added to the mixture and further stirred at 40° C. for 30 minutes. To the resulting mixture was further added 26 g (0.25 mol) of 35% hydrochloric acid. After being stirred at 40° C., 60 g (1 mol) of acetic acid was further added to the mixture and stirred at 40° C. for 30 minutes. The resulting mixture was thermally hydrolyzed at 90° C. for 3 hours.

Next, after the resulting sol was filtered, the filtration residue was dispersed in 500 mL of 1.5 mol/L hydrochloric acid with an ultrasonic disperser, stirred at 90° C. for 3 hours, neutralized with sodium hydroxide, and then filtered. The filtration residue was washed with water and dried to obtain an anatase titanium oxide powder.

SEM observations showed that the powder obtained was porous pseudospherical particles having a mean particle size of about 60 nm, which had been formed by the aggregation of primary particles of titanium oxide.

Comparative Production Example 1

This example was produced without adding sodium hydroxide and hydrochloric acid in Production Example 2. More specifically, to 1 L of a 1 mol/L aqueous solution of titanium tetrachloride was added 92 g (1 mol) of glycerin, and the resulting mixture was stirred at 40° C. The resulting mixture was thermally hydrolyzed at 90° C. for 3 hours.

Next, after the resulting sol was filtered, the filtration residue was dispersed in 500 mL of 1.5 mol/L hydrochloric acid with an ultrasonic disperser, stirred at 90° C. for 3 hours, neutralized with sodium hydroxide, and then filtered. The filtration residue was washed with water and dried to obtain a rutile titanium dioxide powder.

SEM observations showed that the powder obtained was porous pseudospherical particles having a mean particle size of about 90 nm, which had been formed by the aggregation of primary particles of titanium oxide.

Comparative Production Example 2

This example was produced without adding glycerin in Production Example 2. More specifically, 1 L of a 1 mol/L aqueous solution of titanium tetrachloride was stirred at 40° C., 10 g (0.25 mol) of sodium hydroxide was added thereto and further stirred at 40° C. for 30 minutes. To the resulting mixture was further added 26 g (0.25 mol) of 35% hydrochloric acid. After being stirred at 40° C. for 30 minutes, the resulting mixture was thermally hydrolyzed at 90° C. for 3 hours.

Next, after the resulting sol was filtered, the filtration residue was dispersed in 500 mL of 1.5 mol/L hydrochloric acid with an ultrasonic disperser stirred at 90° C. for 3 hours, neutralized with sodium hydroxide, and then filtered. The filtration residue was washed with water and dried to obtain a rutile titanium dioxide powder.

SEM observations showed that the powder obtained was nonporous amorphous particles having a mean particle size of about 2 μm, which had been formed by the aggregation of primary particles of titanium oxide.

Test Example 1

Transparency and Ultraviolet Protective Effect

The transmittance of the porous titanium oxide powders of Production Examples 1 to 5 and Comparative Production Examples 1 to 2 was measured by using the following method to evaluate the transparency in the visible region and the ultraviolet protective effect.

More specifically, 2 g of each powder was thoroughly ground and dispersed in 3 g of castor oil with three-roll mill, and the dispersion obtained was further diluted with caster oil to a powder content of 5 wt %. This dispersion was applied to a quartz glass to form a 5-μm thick layer thereon and dried at room temperature for 30 minutes. The transmittance of the formed coating film at 280 to 800 nm was measured with a spectrophotometer and evaluated based on the following criteria.

<Criteria for Evaluation of Transparency in the Visible Region>

⊚: Transmittance at 450 nm is 90% or more

○: Transmittance at 450 nm is 85% or more and less than 90%

Δ: Transmittance at 450 nm is 80% or more and less than 85%

X: Transmittance at 450 nm is less than 80%

<Criteria for Evaluation of Ultraviolet Protective Effect>

⊚: Transmittance at 280 nm is less than 5%

○: Transmittance at 280 nm is 5% or more and less than 10%

Δ: Transmittance at 280 nm is 10% or more and less than 15%

X: Transmittance at 280 nm is 15% or more

TABLE 1

| Test Powder | Conditions for Thermal Hydrolysis | Heat Treatment with acid | Transparency | UV Protective Effect |
|---|---|---|---|---|
| Production Ex. 1 | polyalcohol + alkali + acid(HCl) | not conducted | ○ | ○ |
| Production Ex. 2 | polyalcohol + alkali + acid(HCl) | conducted | ⊚ | ⊚ |
| Production Ex. 3 | polyalcohol + alkali | conducted | ⊚ | ○ |
| Production Ex. 4 | polyalcohol + alkali + acid(acetic acid) | conducted | ⊚ | ○ |
| Production Ex. 5 | polyalcohol + alkali + acid(HCl + acetic acid) | conducted | ⊚ | ○ |
| Comp. Production Ex. 1 | polyalcohol | conducted | ○ | Δ |
| Comp. Production Ex. 2 | alkali + acid(HCl) | conducted | X | X |

In the cases where a titanium salt solution was thermally hydrolyzed and then further heat treated with an acid, as shown in Table 1, the addition of an alkali or both an alkali and an acid to a polyalcohol-containing titanium salt solution (Production Examples 2 to 5) more improved the transparency and ultraviolet protection, compared to no addition of alkali and acid (Comparative Production Example 1). Especially, the ultraviolet protective effect became very strong by adding the alkali and then hydrochloric acid (Production Examples 2 and 5).

In contrast, when only an alkali and an acid were added without using any polyalcohol, both the transparency and the ultraviolet protection were very low.

In addition, when an alkali and an acid were added to a polyalcohol-containing titanium salt solution and this solution was then thermally hydrolyzed, higher transparency and ultraviolet protection were obtained without subsequent acid heat treatment than in Comparative Production Example 1 (Production Example 1).

FIG. 1 is a photomicrograph of Production Example 2 observed under a scanning electron microscope (SEM) as the porous titanium oxide powder according to the present invention. As shown in FIG. 1, the porous titanium oxide powder particle according to the present invention is pseudospherically formed by the aggregation of primary particles of titanium oxide.

In the following, cosmetics containing the porous titanium oxide powder according to the present invention is explained. The content is expressed in mass percent.

| Formulation Example 1 O/W milky lotion-type sunscreen | | |
|---|---|---|
| 1. | Porous titanium oxide powder (Production Example 2) | 10 |
| 2. | Zinc white | 5 |
| 3. | Stearic acid | 2 |
| 4. | Cetyl alcohol | 1 |
| 5. | Petrolatum | 5 |
| 6. | Silicone oil | 2 |
| 7. | Liquid paraffin | 10 |
| 8. | Glyceryl monostearate (self-emulsification type) | 1 |
| 9. | Polyoxyethylene (25) monooleate | 1 |
| 10. | Polyethylene glycol 1500 | 5 |
| 11. | VEEGUM | 0.5 |
| 12. | Purified water | 57.5 |
| 13. | Perfume | Q.S. |
| 14. | Antiseptics | Q.S. |

Polyethylene glycol was added to purified water and then dissolved by heating. Zinc white and VEEGUM were added to this solution and uniformly dispersed with a homomixer, and then the resulting dispersion was maintained at 70° C. (aqueous phase). The other ingredients were mixed and dissolved by heating and maintained at 70° C. (oil phase). The oil phase was added to the aqueous phase and uniformly emulsified with a homomixer. The resulting emulsion was cooled to 35° C. while being stirred to obtain an O/W milky lotion-type sunscreen.

As a comparative example, a sunscreen was produced in a similar way by using the porous titanium oxide powder of Comparative Production Example 1 instead of the porous titanium oxide powder of Production Example 2 (Comparative Formulation Example 1).

A 10-member expert panel conducted a usability test and reported that Formulation Example 1 was more highly rated than Comparative Formulation Example 1 in terms of feeling in use, natural finish and ultraviolet protective effect.

| Formulation Example 2 Powder foundation | | |
|---|---|---|
| 1. | Porous titanium oxide powder (Production Example 1) | 12 |
| 2. | Titanium dioxide-coated mica | 6 |
| 3. | Talc | 15 |
| 4. | Sericite | 25 |
| 5. | Iron oxide | 5 |
| 6. | Spherical nylon powder | 2 |
| 7. | Spherical PMMA powder | 4 |
| 8. | Boron nitride powder | 1 |
| 9. | Mica | to 100 |
| 10 | Polyether-modified silicone | 0.5 |
| 11 | Sorbitan sesquiisostearate | 1 |
| 12. | Liquid paraffin | 3 |
| 13. | Dimethylpolysiloxane | 1 |
| 14. | Petrolatum | 2 |

| Formulation Example 2 Powder foundation | | |
|---|---|---|
| 15. | 2-Ethylhexyl p-methoxycinnamate | 2 |
| 16. | Glyceryl triisooctanoate | 0.5 |
| 17. | Antiseptics | Q.S. |
| 18. | Perfume | Q.S. |

Ingredients 1 to 9 listed above were uniformly mixed and ingredients 10 to 18 dissolved by heating were added thereto. The mixture was uniformly mixed again and put into a container to prepare a powder foundation.

As a comparative example, another powder foundation was produced in a similar way by using the porous titanium oxide powder of Comparative Production Example 2 instead of the porous titanium oxide powder of Production Example 2 (Comparative Formulation Example 2).

A 10-member expert panel conducted a usability test and reported that Formulation Example 2 was more highly rated than Comparative Formulation Example 2 in terms of feeling in use, natural finish and ultraviolet protective effect.

What is claimed is:

1. A process for producing a porous titanium oxide comprising steps of:
    adding an alkali to a titanium salt solution containing a polyalcohol; and
    thermally hydrolyzing the titanium salt solution,
    wherein the alkali is selected from the group consisting of sodium hydroxide, potassium hydroxide, ammonia water and sodium carbonate,
    the titanium salt is selected from the group consisting of titanium sulfate, titanyl sulfate and titanium tetrachloride, and
    the molar ratio of the amount of the alkali added with respect to that of the titanium salt is 0.1:1 to 1:1.

2. The process according to claim 1, wherein after the alkali is added to the titanium salt solution, an acid is further added thereto and then the solution is thermally hydrolyzed.

3. The process according to claim 1, wherein the molar ratio of the amount of the alkali added with respect to that of the titanium salt is 0.1:1 to 1:1.

4. The process according to claim 2, wherein the molar ratio of the amount of the acid added with respect to that of the titanium salt is 0.1:1 to 1:1.

5. The process according to claim 1, wherein after the thermal hydrolysis, a heat treatment with an acid is further conducted.

6. The process according to claim 1, wherein the molar ratio of the amount of the polyalcohol to that of the titanium salt is 0.1:1 to 5:1.

7. The process according to claim 1, wherein the thermal hydrolysis is conducted at a temperature from 50° C. to 100° C.

8. The process according to claim 1, wherein the porous titanium oxide has a mean particle size of 0.01 to 1.0 μm and a specific surface area of 50 $m^2/g$ or more.

9. The process according to claim 1, wherein particles of the porous titanium oxide are formed by aggregation of primary particles of titanium oxide.

* * * * *